(12) United States Patent
Park et al.

(10) Patent No.: US 9,465,912 B2
(45) Date of Patent: Oct. 11, 2016

(54) METHOD AND APPARATUS FOR MINING TEMPORAL PATTERN

(71) Applicant: Samsung Electronics Co., Ltd., Suwon-si (KR)

(72) Inventors: Hyoung-Min Park, Seoul (KR); Hyo-A Kang, Seoul (KR); Ki-Yong Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 357 days.

(21) Appl. No.: 14/267,351

(22) Filed: May 1, 2014

(65) Prior Publication Data

US 2014/0330843 A1 Nov. 6, 2014

(30) Foreign Application Priority Data

May 3, 2013 (KR) ........................ 10-2013-0050247

(51) Int. Cl.
| | | |
|---|---|---|
| *G06F 7/00* | (2006.01) | |
| *G06F 17/30* | (2006.01) | |
| *G06F 19/24* | (2011.01) | |
| *G06F 19/00* | (2011.01) | |
| *G06K 9/68* | (2006.01) | |

(52) U.S. Cl.
CPC ........... *G06F 19/24* (2013.01); *G06F 19/3443* (2013.01); *G06K 9/6892* (2013.01)

(58) Field of Classification Search
None
See application file for complete search history.

(56) References Cited

U.S. PATENT DOCUMENTS

| | | | | |
|---|---|---|---|---|
| 6,092,065 A | * | 7/2000 | Floratos | ............ G06F 17/30985 382/161 |
| 7,440,461 B2 | | 10/2008 | Sahita et al. | |
| 2006/0115146 A1 | * | 6/2006 | Ogura | ................... G06F 19/363 382/159 |
| 2009/0193044 A1 | * | 7/2009 | Buehrer | ............ G06F 17/30861 |
| 2010/0095162 A1 | * | 4/2010 | Inakoshi | ............. G06F 11/3409 714/45 |

FOREIGN PATENT DOCUMENTS

| | | |
|---|---|---|
| KR | 10-2009-0083972 A | 8/2009 |
| KR | 10-1091204 B1 | 12/2011 |

OTHER PUBLICATIONS

Agrawal, Rakesh, et al. "Mining association rules between sets of items in large databases." ACM SIGMOD Conference. vol. 22. No. 2. ACM, 1993. (10 pages).
Agrawal, Rakesh, et al. "Fast algorithms for mining association rules." Proceeding of the 20th VLDB Conference. vol. 1215. 1994. (13 pages).
Han, Jiawei, et al. "Mining frequent patterns without candidate generation." ACM SIGMOD Record. vol. 29. No. 2. ACM, 2000. (12 pages).

(Continued)

*Primary Examiner* — Tuan A Pham
(74) *Attorney, Agent, or Firm* — NSIP Law

(57) ABSTRACT

An apparatus and a method for mining temporal pattern are provided. A method for mining temporal pattern includes generating a data pattern group comprising data patterns from sequential data, generating a candidate pattern group comprising candidate patterns from the data pattern group, calculating a support value for a candidate pattern in a candidate pattern group based on a discrepancy value of the candidate pattern, and determining whether the candidate pattern satisfies a predetermined pattern requirement, based on the calculated support value.

18 Claims, 9 Drawing Sheets

(56) References Cited

OTHER PUBLICATIONS

Cong, Gao, et al. "Mining top-k covering rule groups for gene expression data." Proceedings of the 2005 ACM SIGMOD international conference on Management of data. ACM, 2005. (60 pages)

Cheng, Hong, et al. "Direct discriminative pattern mining for effective classification." Data Engineering, 2008. ICDE 2008. IEEE 24th International Conference on. IEEE, 2008. (10 pages).

Floratou, Avrilia, et al. "Efficient and Accurate Discovery of Patterns in Sequence Data Sets." Knowledge and Data Engineering, IEEE Transactions, 461-472. (2010).

Négrevergne, Benjamin, et al. "Discovering closed frequent itemsets on multicore: Parallelizing computations and optimizing memory accesses." High Performance Computing and Simulation (HPCS), 2010 International Conference on. IEEE, 2010. (8 pages)

Floratou, Avrilia, et al. "Efficient and Accurate Discovery of Patterns in Sequence Data Sets." Knowledge and Data Engineering, IEEE Transactions on vol. 23 No. 8 (2011) (12 pages).

\* cited by examiner

FIG. 3A

| ID | Sequence |
|----|----------|
| 1  | abcca    |
| 2  | aabca    |
| 3  | bcabc    |
| 4  | ababc    |

METHOD AND APPARATUS FOR MINING TEMPORAL PATTERN

CROSS-REFERENCE TO RELATED APPLICATION(S)

This application claims the benefit under 35 USC 119(a) of Korean Patent Application No. 10-2013-0050247 filed on May 3, 2013, in the Korean Intellectual Property Office, the entire disclosure of which is incorporated herein by reference for all purposes.

BACKGROUND

1. Field

The following description relates to a method and an apparatus for mining temporal pattern.

2. Description of Related Art

With the development of a variety of medical equipment and the introduction of a computerized system, the amount of medical data produced in hospitals is increasing explosively. The flood of medical data is beyond the analytical capabilities of physicians. For example, biometric data, such as electrocardiograms (ECG or EKG) obtained by electrocardiography, is obtained per second, and thus the amount of data generated per day is significantly large. As a result, researches on techniques related to data mining for analysis of large data are on the rise.

An interest pattern model that defines a shape of a pattern of interest is applied in some data mining techniques. Frequent patterns in sequential data may be extracted using the interest pattern model that specifies an intended pattern length, a maximum discrepancy value, and a minimum support value.

However, by extracting data that meet the maximum permissible discrepancy value, patterns that do not actually appear in the sequential data may be also extracted. In addition, an increase in the maximum permissible discrepancy value may result in an increase in the number of frequent patterns, which makes the data analysis computationally challenging. Thus, an effective data mining technique capable of preventing unnecessary patterns from being extracted and capable of providing an increased mining speed is desirable.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method for mining temporal pattern based on an interest pattern model includes generating a data pattern group comprising data patterns with a same length, generating a candidate pattern group comprising candidate patterns based on the data pattern group, each candidate pattern of the candidate pattern group having discrepancy values equal to or smaller than a maximum discrepancy value of the interest pattern model, with respect to each data pattern in the data pattern group, calculating a support value for each candidate pattern in the candidate pattern group by applying a weight varying based on the discrepancy value with respect to each data pattern of the data pattern group, and determining whether each candidate pattern satisfies a predetermined pattern requirement, based on the calculated support value for a corresponding candidate pattern.

The data pattern group may be generated based on a data suffix tree for sequential data.

The predetermined pattern requirement may include at least one of: (1) a support value for a corresponding candidate pattern being greater than a minimum support value of the interest pattern model, and (2) a frequency of a data pattern with discrepancy value of 0 with respect to the candidate pattern being equal to or greater than a preset threshold.

The general aspect of the method may further include eliminating a candidate pattern that does not satisfy the predetermined pattern requirement from the candidate pattern group.

The general aspect of the method may further include, in response to a determination that a length of a candidate pattern is not identical to an intended pattern length of the interest pattern model, eliminating a data pattern, whose discrepancy values with respect to each of the other candidate patterns in the candidate pattern group are all greater than the maximum discrepancy value, from the data pattern group; and generating a new data pattern group by combining remaining data patterns, after the elimination, with a pattern unit based on the data suffix tree.

The generating of the candidate pattern group may include generating a candidate pattern group comprising only some candidate patterns among all possible candidate patterns according to an available memory size.

The calculating of the support value for each candidate pattern may include calculating the support value for each candidate pattern based on information about a number of sequential data.

The general aspect of the method may further include generating the data suffix tree based on an inputted sequential data.

In another general aspect, an apparatus for mining temporal pattern based on an interest pattern model includes a data pattern generator configured to generate a data pattern group comprising data patterns with a same length, a candidate pattern generator configured to generate a candidate pattern group comprising candidate patterns, each candidate pattern of the candidate pattern group having discrepancy values with respect to each data pattern in the data pattern group being smaller than a maximum discrepancy value of the interest pattern model, a support calculator configured to calculate a support value for each candidate pattern in the candidate pattern group by applying a weight varying based on the discrepancy value with respect to each data pattern of the data pattern group, and a controller configured to determine whether each candidate pattern satisfies a predetermined pattern requirement, based on the calculated support value for corresponding candidate pattern.

The pattern group may be generated based on a data suffix tree for sequential data.

The predetermined pattern requirement may include at least one of: (1) a support value for a corresponding candidate pattern being greater than a minimum support value of the interest pattern model, and (2) a frequency of a data pattern with discrepancy value of 0 with respect to the candidate pattern being equal to or greater than a preset threshold.

The controller may be configured to eliminate a candidate pattern that does not satisfy the predetermined pattern requirement from the candidate pattern group.

The controller may be configured to eliminate a data pattern, whose discrepancy value with respect to each of remaining candidate patterns within the candidate pattern group are all greater than the maximum discrepancy value, from the data pattern group.

The controller may be configured to, in response to a determination that a length of a candidate pattern within the candidate pattern group is not identical to an intended pattern length of the interest pattern model, generate a new data pattern group by combining data patterns in the data pattern group with a pattern unit, based on the data suffix tree.

The support calculator may be configured to calculate the support value for each candidate pattern in the candidate pattern group based on information about a number of the sequential data.

The general aspect of the apparatus may further include a data suffix tree generator configured to generate the data suffix tree based on inputted sequential data.

In another general aspect, a method for mining temporal pattern includes generating a data pattern group comprising data patterns from sequential data, generating a candidate pattern group comprising candidate patterns from the data pattern group, calculating a support value for a candidate pattern in a candidate pattern group based on a discrepancy value of the candidate pattern with respect to a data pattern, and determining whether the candidate pattern satisfies a predetermined pattern requirement, based on the calculated support value.

The calculating of the support value may include calculating the support value by applying a weight to the discrepancy value of the candidate pattern.

The general aspect of the method may further include removing the candidate pattern from the candidate pattern group in response to a determination that the candidate pattern fails to satisfy the predetermined pattern requirement.

Other features and aspects will be apparent from the following detailed description, the drawings, and the claims.

BRIEF DESCRIPTION OF THE DRAWINGS

FIG. 3A is a table including an example of sequential data.

Figure 1:
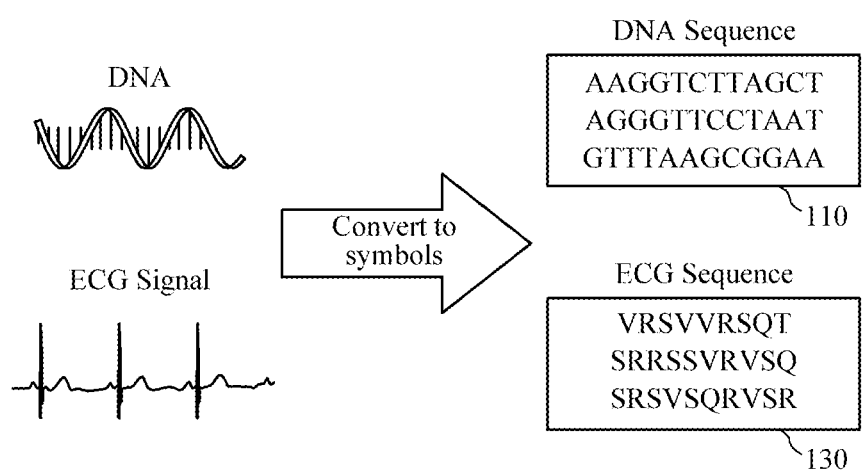
FIG. 1 is a diagram illustrating an example of sequential data.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating examples of sequential data.

Referring to FIG. 1, sequential data refers to a series of data in which successive events are arranged according to a particular rule. For example, sequential data may be a symbolized representation of a DNA sequence 110. In another example, the sequential data may be symbolized representation of an electrocardiogram measurement data 130. The sequential data may be serial data in which particular words, letters, or numbers are enumerated; however, aspects of the present disclosure are not limited thereto.

A "pattern unit" refers to a unit of minimum size that forms the sequential data. For example, the DNA sequence 110 illustrated in FIG. 1 includes A, G, T and C as pattern units. In addition, a "pattern" refers to a sequential combination of the pattern units.

An interest pattern model may include an intended pattern length, a maximum discrepancy value, and a minimum support that are set in advance for mining a desired pattern from sequential data.

A "pattern of interest" refers to a pattern having a length that satisfies an intended pattern length, in which the pattern is calculated by taking into account the maximum permissible discrepancy value (or maximum discrepancy value) of the interest pattern model, and has a support value for the pattern that is greater than the minimum required support value.

A "frequency" refers to the number of occurrences of a particular pattern in sequential data, and a sequence that includes the particular pattern is regarded as supporting the particular pattern. In addition, a "frequency" does not reflect a discrepancy value, but a "support value" for a particular pattern is a value that indicates a degree of support for the particular pattern that is determined based on a discrepancy value with another pattern, which will be described later.

The "discrepancy value" is used to calculate a support value for a particular pattern, allowing a similar pattern to be taken into account in the calculation, so as to reduce noises that may be generated in the process of obtaining sequential data. The discrepancy value is generated in response to two compared patterns with the same length having a different pattern unit located at the same position of the same length. For example, when pattern "abc" and pattern "adc" are compared to each other, a discrepancy value is 1 because a different pattern unit "b" and "d" is located at the same position of each pattern while other positions of the two patterns having the same value.

In one example, anti-monotonicity may be used to reduce a pattern exploration area. In applying anti-monotonicity, a pattern unit with a length of 1 is determined as to whether it satisfies a criterion, and a determination is continuously made as to whether or not each of the patterns generated by increasing the length by 1 to a desired length L satisfies the criterion. During this process, anti-monotonicity may be used to reduce the exploration area.

Figure 2:
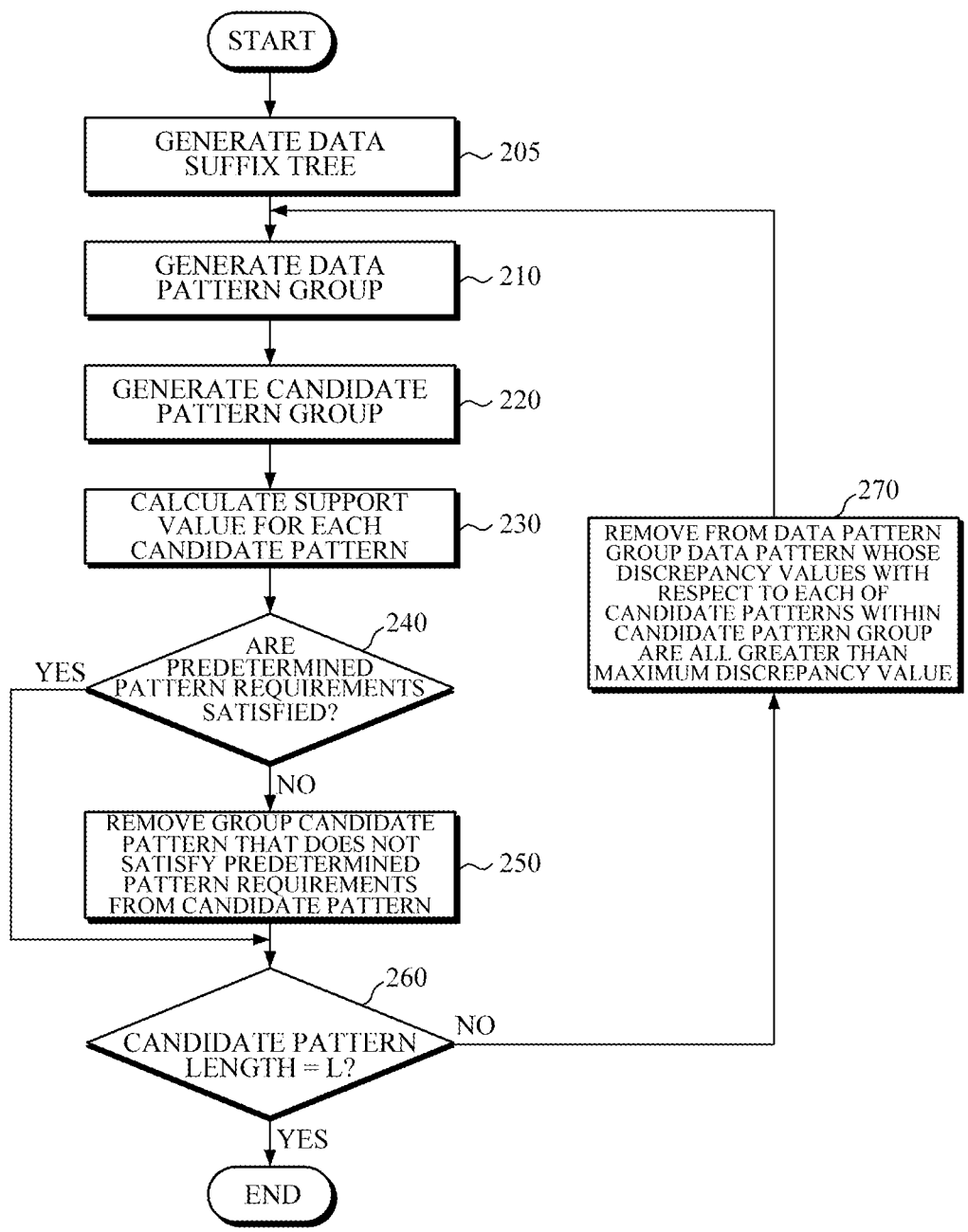
FIG. 2 is a flowchart illustrating an example of a method for mining a temporal pattern.

FIG. 2 illustrates an example of a method for mining a temporal pattern.

Referring to FIG. 2, in 210, a group of data patterns is generated based on a data suffix tree of sequential data. For example, a group of data patterns with the same pattern length may be created based on information at each node of the data suffix tree.

Thereafter, in 220, a candidate pattern group is created using the generated group of data patterns.

In one example, a candidate pattern group consisting of candidate patterns with discrepancy values that fall within the maximum discrepancy value of an interest pattern model is created based on a group of data patterns generated from a data suffix tree. In the candidate pattern group, each candidate pattern has a discrepancy value obtained with respect to each data pattern that belonged to the group of generated data patterns. For example, assuming that the maximum discrepancy value according to the interest pattern model is 1, a pattern unit group consisting of pattern units in sequential data is {a, b, c} and a data pattern group is {ab, ac}. A candidate pattern group with a discrepancy value of 1 or smaller, with respect to data pattern "ab," is {aa, ab, ac, bb, cb}. A candidate pattern group with a discrepancy value of 1 or smaller, with respect to data pattern "ac," is {aa, ab, ac, bc, cc}. Thus, a candidate pattern group generated based on data pattern group {ab, ac} becomes {aa, ab, ac, bb, bc, cb, cc}.

In 230, a support value for each candidate pattern in the candidate pattern group is calculated.

The support value may be calculated by taking into account a discrepancy value with respect to each data pattern, based on a frequency of each data pattern. In this example, a different weight is applied to the discrepancy value with respect to each data pattern in calculating a support value for a candidate pattern. This process can be represented by Equation 1 as follows:

$$P \text{ Support} = \Sigma w_j \times \text{Frequency of } S \text{ supporting } P \quad (1)$$

In Equation 1, P denotes a candidate pattern, S denotes a data pattern, j denotes a discrepancy value between candidate pattern P and data pattern S, and $W_j$ denotes a weight when the discrepancy value is j.

In an example, for a candidate pattern group having values of $W_0$=0.9, $W_1$=0.1, "ab" and "bb" are data patterns that support candidate pattern "ab" as the data patterns have discrepancy values with respect to candidate pattern "ab" that fall within the maximum discrepancy value of an interest pattern model. A frequency of data pattern "ab" is 5, and a frequency of data pattern "bb" is 3. A support value for candidate pattern "ab" is 0.9*5+0.1*3=4.3.

In another example, a support value may be calculated based on the number of inputted sequential data. A significance of a data pattern having a frequency of occurrence of 10 in a set of 100 sequential data and a significance of a data pattern having a frequency of occurrence of 10 in a set of 10 sequential data may be different. Accordingly, a support value for a candidate pattern may be calculated based on the number of sequential data in an inputted sequential data set. In this example, the support value is calculated based on Equation 2 as follows:

$$P \text{ Support} = \sum w_j \times \frac{\text{Frequency of } S \text{ supporting } P}{x} \quad (2)$$

In Equation 2, x denotes the number of inputted sequential data sets.

Based on the calculated support value for each candidate pattern, it is determined whether the candidate pattern satisfies predefined pattern requirements in 240. For example, the pattern requirements may include a criterion that a support value for the candidate pattern is equal to or greater than a minimum support value of an interest pattern model (requirement 1), or a criterion that a frequency of the data pattern whose discrepancy value with respect to the candidate pattern is 0 is equal to or greater than a preset threshold (requirement 2). However, the pattern requirements are not limited thereto, and information gain criteria for mining discriminative patterns or other various criteria for mining robust patterns may be included in the requirements. In addition, in requirement 2, a threshold for a frequency of a data pattern may be set according to the discrepancy value. For example, a threshold for a frequency of a data pattern with a discrepancy value of 0, a threshold for a frequency of a data pattern with a discrepancy value of 1, and a threshold for a frequency of a data pattern with a discrepancy value of 2 may be individually set in requirement 2. In addition, so as to meet the requirement, the frequency of the data pattern may be required to be equal to or greater than the corresponding threshold according to the discrepancy value.

Then, in response to a determination made in 240, a candidate pattern that does not meet the predefined pattern requirements is eliminated from a candidate pattern group in 250.

Thereafter, it is determined whether a length of the candidate patterns remaining in the candidate pattern group is identical to an intended pattern length in the interest pattern model in 260.

In response to a determination made in 260 that the length of the candidate pattern is identical to the intended pattern length, the candidate pattern is extracted from the candidate pattern group, and the process is terminated.

In response to a determination made in 260 that the length of the candidate pattern is not identical to the intended pattern length, a data pattern, whose discrepancy values with respect to each of the remaining candidate patterns remaining in the candidate pattern group all exceed the maximum discrepancy value of the interest pattern model, is eliminated from the data pattern group in 270. The data patterns remaining in the data pattern group are combined with a pattern unit based on a data suffix tree to generate a new pattern group in 210. That is, the data pattern that does not support the remaining candidate patterns is eliminated from the data pattern group, and the remaining data patterns are combined with the pattern unit to generate a new data pattern group.

In response to a determination made in 240 that all candidate patterns that belong to the candidate pattern group satisfy the predefined pattern requirements, it is determined whether the length of the candidate patterns in the candidate pattern group is identical to the intended pattern length of the interest pattern model in 260.

In another example, a method for mining temporal pattern may further include receiving sequential data sets and generating a suffix tree based on the received sequential data sets in 250.

In 220, the candidate pattern group is generated to include only some candidate patterns among all possible candidate patterns. The determination as to which candidate patterns are included in the candidate pattern group may be based on a memory size, and a pattern search may be performed on the generated candidate pattern group. Then, after finishing the pattern search on the candidate pattern group, another candidate pattern group may be generated to include the remaining candidate patterns. Another pattern search may be performed of the newly generated candidate pattern group. Thus, even with a small available memory size, a quick search is possible by appropriately adjusting the pattern search range according to the memory size.

In one example, for mining a desired pattern from sequential data, an interest pattern model that includes an intended pattern length, minimum similarity, and a minimum support value may be used. The similarity takes into account a length of a pattern and may be defined as a value obtained by dividing a discrepancy value between two patterns by the length of the pattern. For example, if the similarity between two patterns is less than the minimum similarity, it may be determined that both patterns are similar to each other, and it may be determined that the minimum similarity requirement of the interest pattern model is satisfied.

Hereinafter, an example of a method for mining temporal pattern will be described with reference to FIGS. 3A to 3F.

Figure 3A:
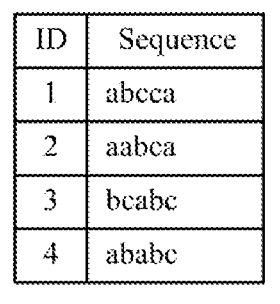
Figure 3B:
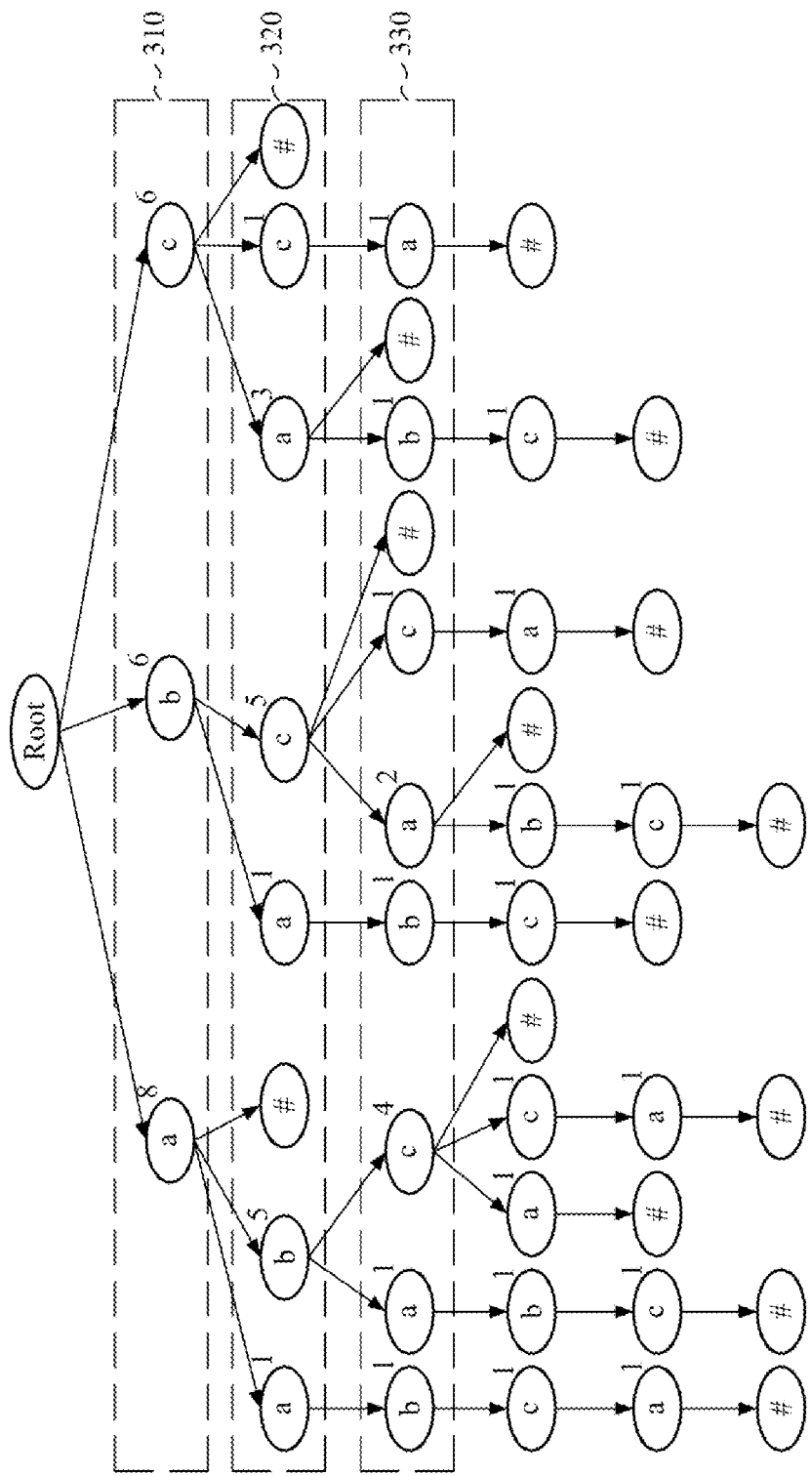
FIG. 3B is a diagram illustrating an example of a data suffix tree.
Figure 3C:
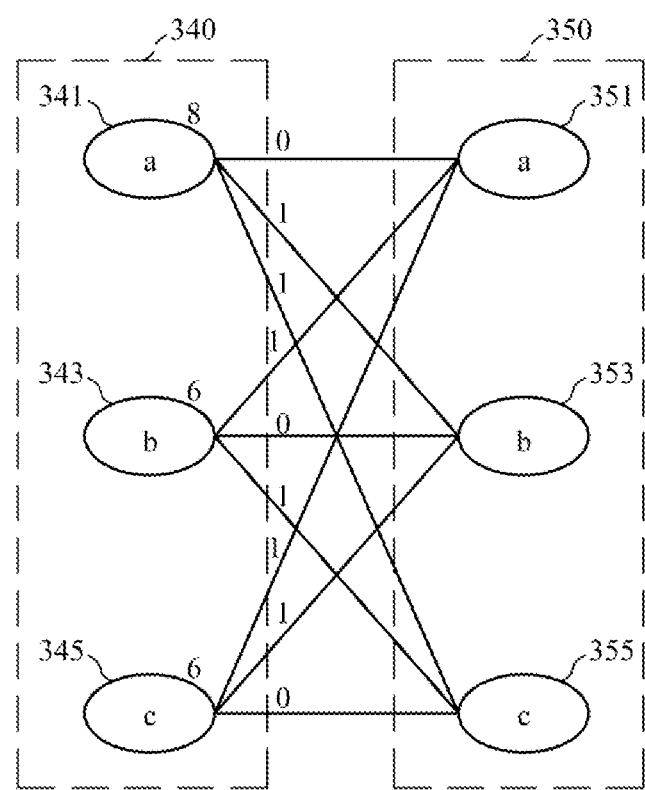
FIG. 3C is a diagram illustrating an example of a bipartite graph with a data pattern group of data patterns with a length of 1 and a candidate pattern group of candidate patterns with a length of 1.
Figure 3D:
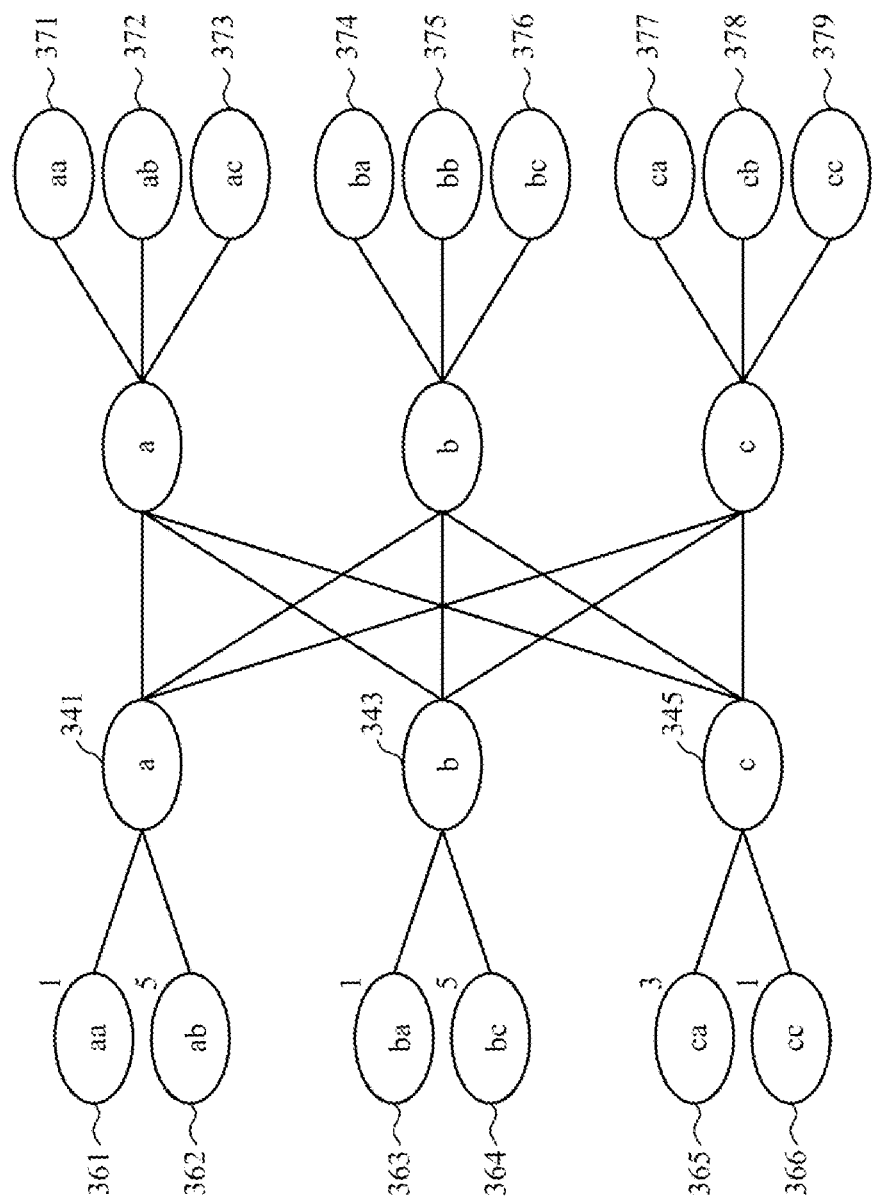
FIG. 3D is a diagram illustrating an example of a bipartite graph with a data pattern group of data patterns with a length of 2 and a candidate pattern group of candidate patterns with a length of 2.
Figure 3E:
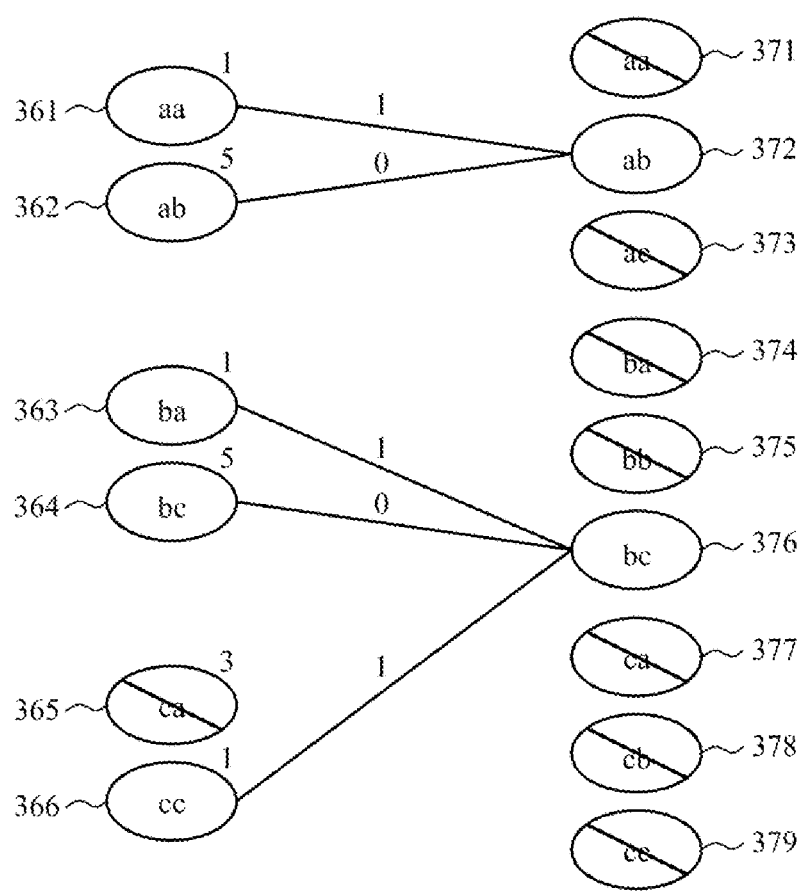
FIG. 3E is a diagram illustrating an example of a bipartite graph with data patterns with a length of 2.
Figure 3F:
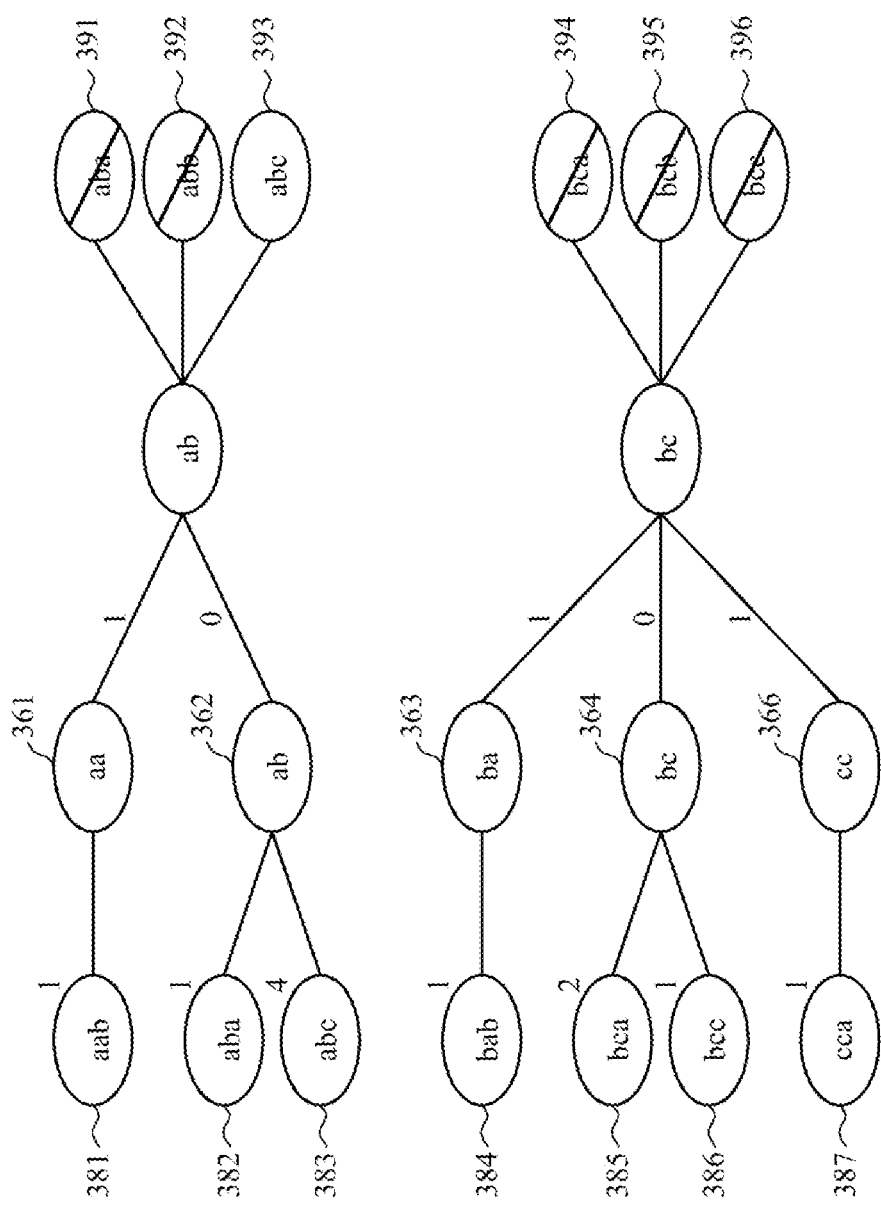
FIG. 3F is a diagram illustrating an example of a bipartite graph with a data pattern group of data patterns with a length of 3 and a candidate pattern group of candidate patterns with a length of 3.

FIG. 3A illustrates an example of an inputted sequential data, and FIG. 3B illustrates an example of a data suffix tree generated based on the sequential data of FIG. 3A. FIG. 3C illustrates a bipartite graph including a data pattern group of data patterns with a length of 1 and a candidate pattern group of candidate patterns with a length of 1. FIG. 3D illustrates a bipartite graph including a data pattern group of data patterns with a length of 2 and a candidate pattern group of candidate patterns with a length of 2. FIG. 3E illustrates a bipartite graph including data patterns, with a length of 2, which are directly connected to the candidate patterns with a length of 2 in the bipartite graph of FIG. 3D. FIG. 3F illustrates a bipartite graph including a data pattern group of data patterns with a length of 3 and a candidate pattern group of candidate patterns with a length of 3.

In the example of a method for mining temporal pattern illustrated in FIGS. 3A to 3F, an interest pattern model is set to have 3 as an intended pattern length, 1 as a maximum discrepancy value, and 3.2 as a minimum support value. A weight of 0.8 ($w_0$=0.8) is applied to the calculation of a support value when a discrepancy value is 0. A weight of 0.1 ($w_1$=0.2) is applied to the calculation of a support value when a discrepancy value is 1. The number of sequential data sets is not taken into account in calculating a support value. Further, it is assumed that a support value of a given pattern needs to be equal to or greater than a minimum support value (requirement 1) to meet the predefined pattern requirements.

To facilitate the creation of a candidate pattern and the calculation of a support value, a bipartite graph is used. The left side of the bipartite graph shows nodes corresponding to data patterns generated based on a data suffix tree, and the right side of the bipartite graph shows nodes corresponding to candidate patterns generated based on data patterns. In this example, an edge between two nodes is present when a discrepancy between two patterns is smaller than a maximum discrepancy value and each edge may store the discrepancy value.

In response to the input of a set of sequential data illustrated in FIG. 3A, a data suffix tree such as the example illustrated in FIG. 3B is generated based on the inputted sequential data set in 205. At each node of the data suffix tree, a frequency of a pattern corresponding to the node may be stored.

Then, based on the first nodes 310 of the data suffix tree, a data pattern group S1 consisting of data patterns with a length of 1 is generated in 210. A candidate pattern group P1 consisting of candidate patterns, each candidate pattern having a discrepancy value of 1 or smaller with respect to each data pattern within the data pattern group S1, is generated in 220. Referring to FIG. 3C, nodes 340 at the left side of the bipartite graph correspond to data patterns, and nodes 350 at the right side correspond to candidate patterns. In this example, each node at the left side, corresponding to each data pattern, may store a frequency of the corresponding data pattern. Hereinafter, for convenience of explanation, a node of the bipartite graph and a pattern corresponding to the node will be referred to by the same reference numeral.

In the example, a data pattern group S1, {a, b, c}, is generated based on the first nodes 310 in the data suffix tree, and a candidate pattern group P1, {a, b, c} with a discrepancy value of 1 or smaller is generated based on the data pattern group S1.

Then, a support value for each of the candidate patterns within the candidate pattern group P1 is calculated in 230. In the example illustrated in FIG. 3C, given that data patterns that support candidate pattern "a" 351 are data pattern "a" 341, data pattern "b" 343, and data pattern "c" 345, and frequencies of the respective data patterns "a," "b," and "c" are 8, 6, and 6, respectively, the support value for candidate pattern "a" 351 may be calculated as (8*0.8)+(6*0.2)+(6*0.2)=8.8, using Equation 1. In a similar manner, a support value for candidate pattern "b" 353 is (8*0.2)+(6*0.8)+(6*0.2)=7.6 and a support value for candidate pattern "c" 355 is (8*0.2)+(6*0.2)+(6*0.8)=7.6.

Thereafter, it is determined whether each candidate pattern 351, 353, and 355 in the candidate pattern group P1 satisfies a predefined pattern requirement in 240. In this example, the candidate patterns 351, 353, and 355 all satisfy requirement 1 that requires the minimum support value of the interest pattern model to be set to 3.2.

After a determination is made that each candidate pattern 351, 353, and 355 in the candidate pattern group P1 satisfies the predefined pattern requirement, it is further determined whether a length of each candidate pattern 351, 353 and 353 is identical to the intended pattern length included in the interest pattern model in 260. In this example, the length of each candidate pattern is 1, and thus is not identical to the intended pattern length, which is 3.

Because the length of each candidate pattern is different from the intended pattern length, data patterns whose discrepancy value with respect to each candidate pattern that belongs to the candidate pattern group P1 exceeds the maximum discrepancy value are eliminated from the data pattern group S1 in 270. In this example, there is no data pattern that has a discrepancy value that exceeds the maximum discrepancy value of 1 with respect to each candidate pattern 351, 353, and 355 in the candidate pattern group P1.

Then, in 210, based on second nodes 320 in the data suffix tree, a new data pattern group S2 is generated by combining each data pattern 341, 343 and 345 in the data pattern group S1 with an additional pattern unit. In the example illustrated in FIG. 3D, the new data pattern group S2 that consists of data patterns with a length of 2 is generated as {aa, ab, ba, bc, ca, cc} by combining the data patterns 341, 343, and 345 with an additional pattern unit based on the second nodes 320 of the data suffix tree.

Using the data pattern group S2, a candidate pattern group P2 that satisfies the maximum discrepancy value of 1 is generated in 220. In this example, the new candidate pattern group P2 may be generated based on the existing candidate pattern group P1, by using the data pattern group S2.

In this example, due to the maximum discrepancy value of 1, the candidate pattern group P2 generated by using the data pattern group S2 becomes {aa, ab, ac, ba, bb, bc, ca, cb, cc} as illustrated in FIG. 3D.

Then, in 230, a support value for each candidate pattern in the candidate pattern group P2 is calculated. Given that data patterns that support candidate pattern "aa" 371 are "aa" 361, "ab" 362, "ba" 363, and "ca" 365, and frequencies of the respective patterns "aa" 361, "ab" 362, "ba" 363, and "ca" 365 are 1, 5, 1 and 3, respectively, a support value for candidate pattern "aa" 371 may be calculated as (1*0.8)+(5*0.2)+(1*0.2)+(3*0.2)=2.6 by using Equation 1. In the same manner, a support value for candidate pattern "ab" 372 is calculated as 4.2. A support value for candidate pattern "ac" 373 is calculated as 2.4. A support value for candidate pattern "ba" 374 is calculated as 2.6. A support value for candidate pattern "bb" 375 is calculated as 2.2. A support value for candidate pattern "bc" 376 is calculated as 4.4. A support value for candidate pattern "ca" 377 is calculated as 3.0. A support value for candidate pattern "cb" 378 is calculated as 1.8. A support value for candidate pattern "cc" 379 is calculated as 2.4.

In 240, it is determined whether each candidate pattern 371 to 379 within the candidate pattern group P2 satisfies the predetermined pattern requirement. In this example, candidate pattern "ab" 372 and candidate pattern "bc" 376 satisfy requirement 1 that requires the minimum support value of the interest pattern model to be 3.2.

In 250, candidate patterns 371, 373, 374, 375, 377, 378, and 379 that do not satisfy the predetermined pattern requirement are eliminated from the candidate pattern group P2. After eliminating the candidate patterns that do not meet the requirement, a subset {ab, ba} remains as the resulting candidate pattern group P2'.

A length of each candidate pattern is compared to the intended pattern length, and in 260, a determination is made as to whether the length of each candidate pattern is identical to the intended pattern length. In this example, the length of the candidate pattern is 2, and the intended pattern length is 3. Thus, data pattern "ca" 365 has a discrepancy value that exceeds the maximum discrepancy value with respect to each of the candidate patterns "ab" 372 and "ba" 376 within the candidate pattern group P2', and is eliminated from the data pattern group S2 in 270. In the illustrated example, after the elimination of data pattern "ca" 365, the resulting data pattern group S2' includes {aa, ab, ba, bc, cc} as illustrated in FIG. 3E.

Thereafter, in 210, based on the third nodes 330 of the data suffix tree, a data pattern group S3 is generated by combining each data pattern 361, 362, 363, 364 and 366 within the data pattern group S2' with a pattern unit, and a candidate pattern group P3 is generated in 220, which consists of candidate patterns, whose discrepancy values, with respect to each of data patterns 381, 382, 383, 384, 385, 386 and 387 within the data pattern group S3, are smaller than the maximum discrepancy value of 1. The candidate pattern group P3 may be generated based on the candidate pattern group P2'. In this example, the candidate pattern group P3 is {aba, abb, abc, bca, bcb, bcc} as illustrated in FIG. 3F.

In 230, a support value for each of the candidate patterns that belongs to the candidate pattern group is calculated. By using Equation 1, a support value for candidate pattern "aba" 391 is obtained as 1.6. A support value for candidate pattern "abb" 392 is obtained as 1.2. A support value for "abc" 393 is obtained as 3.4. A support value for "bca" 394 is obtained as 2.0. A support value for "bcb" 395 is obtained as 0.8. A support value for "bcc" 396 is obtained as 1.2.

In 240, it is determined whether each candidate pattern satisfies the predetermined pattern requirement. Candidate pattern "abc" 393 is one candidate pattern that satisfies requirement 1, which requires the minimum support value to be 3.2.

In 250, candidate patterns 391, 392, 394, 395 and 396 that do not meet the predetermined pattern requirement are eliminated from the candidate pattern group P3 as illustrated in FIG. 3F. In 260, it is determined whether a length of remaining candidate pattern "abc" 393 is identical to the intended pattern length, which is 3 pattern units. In response to a determination that the length of candidate pattern "abc" 393 is identical to the intended pattern length, the candidate pattern "abc" 393 is determined as a desired pattern to be mined, and the pattern mining process is ceased.

Figure 4:
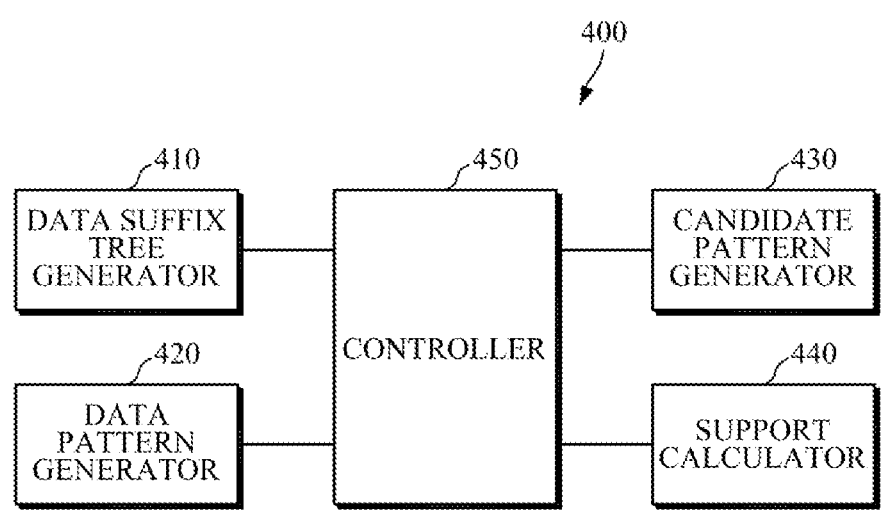
FIG. 4 is a diagram illustrating an example of an apparatus for mining temporal pattern.

FIG. 4 is a diagram illustrating an example of an apparatus for mining temporal pattern. Referring to FIG. 4, the apparatus 400 for mining temporal pattern includes a data suffix tree generator 410, a data pattern generator 420, a candidate pattern generator 430, a support calculator 440, and a controller 450. A data suffix tree generator 410 generates a data suffix tree based on inputted sequential data sets in response to receiving the data set.

The data pattern generator 420 generates a data pattern group based on the data suffix tree generated by the data suffix tree generator 410. For example, the data pattern generator 420 may classify data patterns with the same length into the same group, based on information about each node of the data suffix tree.

The candidate pattern generator 430 uses the data pattern group to generate a candidate pattern group. For example, the candidate pattern generator 430 may generate a candidate pattern group that includes candidate patterns whose discrepancy values, with respect to each of data patterns that belongs to the data pattern group, fall within a maximum discrepancy value of an interest pattern model.

The support calculator 440 calculates a support value for each candidate pattern in the candidate pattern group.

The support value for each candidate pattern may be calculated, based on a frequency of each data pattern, by taking into account a discrepancy value with respect to each data pattern. In this example, depending on the discrepancy value with respect to each data pattern, a different weight is applied to calculate a support value for each candidate pattern. The support value may be calculated by Equation 1 as described above.

In another example, the support value may be calculated by taking into account the number of sequential data in an inputted sequential data set. The significance of a data pattern whose frequency of occurrence is 10 in a set of 100 sequential data and a data pattern whose frequency of occurrence is 10 in a set of 10 sequential data may differ. Accordingly, the number of sequence data in an inputted sequential data set may be used in calculating a support value for a candidate pattern. In this example, the support value is calculated by Equation 2 as described above. The support calculator 440 may be included in a processor.

The controller 450 controls the data suffix tree generator 410, the data pattern generator 420, the candidate pattern generator 430, and the support calculator 440.

The controller 450 may determine whether each candidate pattern satisfies predefined requirements, based on the support value for the candidate pattern. In this example, the predefined pattern requirements include a criteria that a support value for a particular candidate pattern be equal to or greater than a minimum support value of an interest pattern model, which may be referred to as requirement 1, or a criteria that a frequency of a data pattern whose discrepancy value with respect to the candidate pattern is 0 be equal to or greater than a preset threshold, which may be referred to as requirement 2. However, the pattern requirements are not limited thereto, and the information gain requirements for mining discriminative patterns or other various requirements for mining robust patterns may be included in the requirements. For example, as requirement 2, a threshold for a frequency of a data pattern may be set according to the discrepancy value. For instance, a threshold for a frequency of a data pattern with a discrepancy value of 0, a threshold for a frequency of a data pattern with a discrepancy value of 1, and a threshold for a frequency of a data pattern with a discrepancy value of 2 may be set individually. In addition, to meet the requirement, the frequency of the data pattern may be required to be equal to or greater than the corresponding threshold according to the discrepancy value.

The controller 450 eliminates the candidate pattern that does not satisfy the predetermined requirements from the candidate pattern group generated by the candidate pattern generator 430, and may determine whether a length of each candidate pattern remaining in the candidate pattern group is identical to an intended pattern length of the interest pattern model.

In response to a determination made that the length of the remaining candidate pattern is not identical to the intended pattern length, the controller 450 may eliminate a data pattern that only supports the eliminated candidate pattern from the data pattern group, and may control the data pattern generator 420 to generate a new data pattern group by combining the data patterns remaining in the original data pattern after the elimination with a pattern unit, based on the data suffix tree.

The generators or calculators described herein may be implemented using hardware components and software components. For example, the hardware components may include memories, controllers and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. Data may be stored in a memory. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods and/or operations described above may be recorded, stored, or fixed in one or more non-transitory computer-readable storage media that includes program instructions to be implemented by a computer to cause a processor to execute or perform the program instructions. The media may also include, alone or in combination with the program instructions, data files, data structures, and the like. Examples of non-transitory computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

As a non-exhaustive illustration only, an apparatus described herein may refer to a computer, a medical device, a mobile device, a processing device, and the like. The apparatus may be capable of taking biometric measurements. The apparatus may be capable of wired communication, wireless communication or network communication to receive or transmit data. The data may be biometric data.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for mining temporal pattern based on an interest pattern model, the method comprising:
   generating by a processing device a data pattern group comprising data patterns with a same length;
   generating a candidate pattern group comprising candidate patterns based on the data pattern group, each candidate pattern of the candidate pattern group having discrepancy values equal to or smaller than a maximum discrepancy value of the interest pattern model, with respect to each data pattern in the data pattern group;
   calculating a support value for each candidate pattern in the candidate pattern group by applying a weight varying based on the discrepancy value with respect to each data pattern of the data pattern group;
   determining whether each candidate pattern satisfies a predetermined pattern requirement, based on the calculated support value for a corresponding candidate pattern,
   in response to a determination that a length of a candidate pattern is not identical to an intended pattern length of the interest pattern model, eliminating a data pattern, whose discrepancy values with respect to each of the other candidate patterns in the candidate pattern group are all greater than the maximum discrepancy value, from the data pattern group; and
   generating a new data pattern group by combining remaining data patterns, after the elimination, with a pattern unit based on the data suffix tree.

2. The method of claim 1, wherein the data pattern group is generated based on a data suffix tree for sequential data.

3. The method of claim 2, further comprising eliminating a candidate pattern that does not satisfy the predetermined pattern requirement from the candidate pattern group.

4. The method of claim 1, wherein the predetermined pattern requirement comprises at least one of: (1) a support value for a corresponding candidate pattern being greater than a minimum support value of the interest pattern model, and (2) a frequency of a data pattern with discrepancy value of 0 with respect to the candidate pattern being equal to or greater than a preset threshold.

5. The method of claim 1, wherein the generating of the candidate pattern group comprises generating a candidate pattern group comprising only some candidate patterns among all possible candidate patterns according to an available memory size.

6. The method of claim 1, wherein the calculating of the support value for each candidate pattern comprises calculating the support value for each candidate pattern based on information about a number of sequential data.

7. The method of claim 1, further comprising:
   generating the data suffix tree based on an inputted sequential data.

8. An apparatus for mining temporal pattern based on an interest pattern model, the apparatus comprising:
   a processing device configured to generate a data pattern group comprising data patterns with a same length;
   to generate a candidate pattern group comprising candidate patterns, each candidate pattern of the candidate pattern group having discrepancy values with respect to each data pattern in the data pattern group being smaller than a maximum discrepancy value of the interest pattern model;
   to calculate a support value for each candidate pattern in the candidate pattern group by applying a weight varying based on the discrepancy value with respect to each data pattern of the data pattern group; and
   to determine whether each candidate pattern satisfies a predetermined pattern requirement, based on the calculated support value for corresponding candidate pattern,
   in response to a determination that a length of a candidate pattern is not identical to an intended pattern length of the interest pattern model, eliminating a data pattern, whose discrepancy values with respect to each of the other candidate patterns in the candidate pattern group are all greater than the maximum discrepancy value, from the data pattern group; and
   generating a new data pattern group by combining remaining data patterns, after the elimination, with a pattern unit based on the data suffix tree.

9. The apparatus of claim 8, wherein the data pattern group is generated based on a data suffix tree for sequential data.

10. The apparatus of claim 9, wherein the predetermined pattern requirement comprises at least one of: (1) a support value for a corresponding candidate pattern being greater than a minimum support value of the interest pattern model, and (2) a frequency of a data pattern with discrepancy value of 0 with respect to the candidate pattern being equal to or greater than a preset threshold.

11. The apparatus of claim 10, wherein the processing device is configured to eliminate a data pattern, whose discrepancy value with respect to each of remaining candidate patterns within the candidate pattern group are all greater than the maximum discrepancy value, from the data pattern group.

12. The apparatus of claim 9, wherein the processing device is configured to, in response to a determination that a length of a candidate pattern within the candidate pattern group is not identical to an intended pattern length of the interest pattern model, generate a new data pattern group by combining data patterns in the data pattern group with a pattern unit, based on the data suffix tree.

13. The apparatus of claim 9, wherein the processing device is further: configured to generate the data suffix tree based on inputted sequential data.

14. The apparatus of claim 8, wherein the processing device is configured to eliminate a candidate pattern that does not satisfy the predetermined pattern requirement from the candidate pattern group.

15. The apparatus of claim 8, wherein the processing device is configured to calculate the support value for each candidate pattern in the candidate pattern group based on information about a number of the sequential data.

16. A method for mining temporal pattern, the method comprising:
   generating by a processing device a data pattern group comprising data patterns from sequential data;
   generating a candidate pattern group comprising candidate patterns from the data pattern group;
   calculating a support value for a candidate pattern in a candidate pattern group based on a discrepancy value of the candidate pattern with respect to a data pattern;
   determining whether the candidate pattern satisfies a predetermined pattern requirement, based on the calculated support value,
   in response to a determination that a length of a candidate pattern is not identical to an intended pattern length of an interest pattern model, eliminating a data pattern, whose discrepancy values with respect to each of the other candidate patterns in the candidate pattern group are all greater than the maximum discrepancy value, from the data pattern group; and generating a new data pattern group by combining remaining data patterns, after the elimination, with a pattern unit based on the data suffix tree.

17. The method of claim 16, wherein the calculating of the support value comprises calculating the support value by applying a weight to the discrepancy value of the candidate pattern.

18. The method of claim 16, further comprising:

removing the candidate pattern from the candidate pattern group in response to a determination that the candidate pattern fails to satisfy the predetermined pattern requirement.

\* \* \* \* \*